United States Patent
König et al.

Patent Number: 5,389,614
Date of Patent: Feb. 14, 1995

[54] HYDANTOIN DERIVATIVES

[75] Inventors: Wolfgang König, Hofheim; Gerhard Zoller, Schöneck; Melitta Just, Langen; Bernd Jablonka, Bad Soden, all of Germany

[73] Assignee: Cassella AG, Frankfurt am Main, Germany

[21] Appl. No.: 924,745

[22] Filed: Aug. 4, 1992

[30] Foreign Application Priority Data

Aug. 8, 1991 [DE] Germany ............... 4126277

[51] Int. Cl.$^6$ ............. C07D 233/76; C07K 5/02; A61K 37/02
[52] U.S. Cl. ............. 514/18; 514/19; 514/20; 548/319.5
[58] Field of Search ........ 548/319.5; 514/19, 20, 514/18

[56] References Cited

U.S. PATENT DOCUMENTS

| | | | |
|---|---|---|---|
| 4,683,291 | 7/1987 | Zimmerman et al. | 530/330 X |
| 4,857,508 | 8/1989 | Adams et al. | 514/18 |

FOREIGN PATENT DOCUMENTS

| | | | |
|---|---|---|---|
| 449079 | 10/1991 | European Pat. Off. | 548/319.5 |
| 452257 | 10/1991 | European Pat. Off. | 514/18 |
| 462960 | 12/1991 | European Pat. Off. | 514/19 |

OTHER PUBLICATIONS

Lakkakorpi et al., J. Cell. Biol., 115(4), 1179–1186 (1991).
Marguerie et al., J. Biol. Chem., 254(12), 5357–5363 (1979).

Primary Examiner—Robert W. Ramsuer
Assistant Examiner—Fiona T. Powers
Attorney, Agent, or Firm—Perman & Green

[57] ABSTRACT

The invention relates to compounds of the formula I

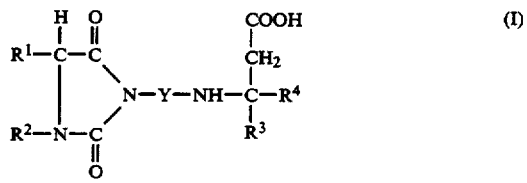

in which $R^1$, $R^2$, $R^3$, $R^4$ and Y have the meanings indicated in Claim 1, to processes for their preparation and their use as active pharmacological substances.

6 Claims, No Drawings

HYDANTOIN DERIVATIVES

BACKGROUND OF THE INVENTION

Hydantoin derivatives are described in European Published Application 449,079, published Oct. 2, 1991. In a further development, we have found that hydantoins of the general formula I also inhibit blood platelet aggregation.

SUMMARY OF THE INVENTION

The present invention therefore relates to compounds of the formula I,

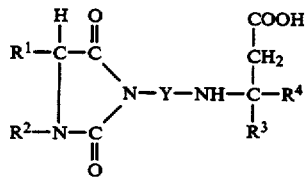

in which
Y denotes —$(CH_2)_m$—CO— or

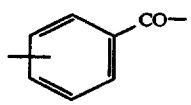

and m represents 1–4;
$R^1$ represents —$(CH_2)_n$—NH—X, —$CH_2$—$C_6H_4$N-H—X, —$CH_2$—$C_6H_4$—C(=NH)—$NH_2$, —$CH_2$—$C_6H_4$—$CH_2$—NH—X or —$C_6H_4$NH—X, or

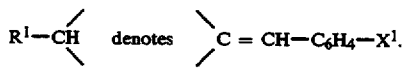

wherein n represents an integer from 3 to 5,
$X^1$ represents —$CH_2NHX$, —NBX or —C(=NH)—$NH_2$,
X represents hydrogen or $C_1$–$C_6$-alkyl, or represents a radical of the formula II,

wherein
R' and R" independently of one another denote hydrogen or $C_1$–$C_6$-alkyl;
$R^2$ denotes hydrogen or $C_1$–$C_6$-alkyl;
$R^3$ denotes hydrogen or a phenyl radical;
$R^4$ denotes hydrogen, $COOR^5$, CO—N($CH_3$)—$R^5$ or CO—NH—$R^5$, wherein
$R^5$ denotes hydrogen, NHCO—$NH_2$ or $C_1$–$C_{18}$-alkyl, which is optionally mono- or polysubstituted by identical or different radicals from the series comprising hydroxyl, carboxyl, carboxamido, amino, mercapto, $C_1$–$C_{18}$-alkoxy, $C_1$–$C_{18}$-alkoxycarbonyl, $C_6$–$C_{14}$-aryl-$C_1$–$C_3$-alkoxycarbonyl, $C_3$–$C_8$-cycloalkyl, halogen, nitro, trifluoromethyl and a radical $R^6$, wherein $R^6$ represents $C_6$–$C_{14}$-aryl, $C_6$–$C_{14}$-aryl-$C_6$–$C_8$-alkyl, or a mono- or bicyclic 5- to 12-membered heterocyclic ring which can be aromatic, partly hydrogenated or completely hydrogenated and can contain, as a hetero element, one, two or three identical or different nitrogen, oxygen or sulphur atoms, the aryl and, independently of one another, the heterocyclic radical optionally being mono- or polysubstituted by identical or different radicals from the series comprising $C_1$–$C_{18}$-alkyl, $C_1$–$C_{18}$-alkoxy, halogen, nitro and trifluoromethyl; or $R^6$ represents a radical $R^7$;

$R^7$ denotes —$NR^8R^9$, —$OR^8$, —$SR^8$ or an amino acid side chain; or a naturally occurring or unnatural amino acid radical, imino acid radical or optionally N—$C_1$–$C_8$-alkylated or $C_5$–$C_{14}$-aryl-$C_1$–$C_8$-alkylated azaamino acid radical or a dipeptide radical, in which the peptide bond can be reduced to NH—$CH_2$, and esters and amides thereof, it being possible for free functional groups optionally to be substituted by hydrogen or hydroxymethyl or protected by protective groups customary in peptide chemistry; or denotes a radical—$COR^{7'}$, wherein $R^{7'}$ is defined as $R^7$;

$R^8$ denotes hydrogen, optionally amino-substituted $C_1$–$C_{14}$-aryl-$C_1$–$C_8$-alkyl, $C_1$–$C_{18}$-alkylcarbonyl, $C_1$–$C_{18}$-alkoxycarbonyl, $C_6$–$C_{14}$-arylcarbonyl, $C_6$–$C_{12}$-aryl-$C_1$–$C_8$-alkylcarbonyl, $C_6$–$C_{18}$-aryl-$C_1$–$C_{18}$-alkoxycarbonyl, or a naturally occurring or unnatural amino acid radical, imino acid radical or optionally N—$C_1$–$C_8$-alkylated or $C_1$–$C_{14}$-aryl-$C_1$–$C_8$-alkylated azaamino acid radical or a dipeptide radical, in which the peptide bond can be reduced to NH—$CH_2$; and $R^9$ denotes hydrogen, $C_1$–$C_{18}$-alkyl, $C_6$–$C_{12}$-aryl or $C_6$–$C_{12}$-aryl-$C_1$–$C_8$-alkyl;

and physiologically tolerated salts thereof, compounds of the formula I wherein simultaneously,
$R^1$ denotes —$(CH_2)_{3-4}$—NH—X, where
X=$C_1$–$C_6$-alkyl or a radical of the formula II;
$R^2$ and $R^3$ denote hydrogen;
$R^4$ denotes —CO—NH—$R^5$ and
Y denotes —$CH_2$—CO being excluded.

Alkyl can be straight-chained or branched. The same applies to radicals derived therefrom, such as, for example, alkoxy, alkanoyl and aralkyl.

Cycloalkyl is also understood as meaning alkyl-substituted radicals, such as, for example, 4-methylcyclohexyl or 2,3-dimethylcyclopentyl.

$C_6$–$C_{14}$-aryl is, for example, phenyl, naphthyl, biphenylyl or fluorenyl; phenyl and naphthyl are preferred. The same also applies to radicals derived therefrom, such as, for example, aryloxy, aroyl, aralkyl and aralkoxy. Aralkyl is understood as being, for example, an unsubstituted or substituted $C_6$–$C_{14}$-aryl radical linked to a $C_1$–$C_8$-alkyl, such as, for example, benzyl, 1- and 2-naphthylmethyl, halobenzyl and alkoxybenzyl, but without aralkyl being limited to the radicals mentioned.

Heterocyclic radicals in the sense of the above definitions are, for example, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindazolyl, indazolyl, phthalazinyl, quinolyl, isoquinolyl, quinoxalinyl, quinazolinyl, cinnolinyl or a benzofused or cyclopenta-, cyclohexa- or cyclohepta-fused derivative of these radicals.

These heterocyclic radicals can be substituted on one nitrogen atom by oxides, $C_1$–$C_7$-alkyl, for example methyl or ethyl, phenyl or phenyl-$C_1$–$C_4$-alkyl, for example benzyl, and/or on one or more carbon atoms by $C_1$–$C_4$-alkyl, for example benzyl, halogen, hydroxyl, $C_1$–$C_4$-alkoxy, for example methoxy, phenyl-$C_1$–$C_4$- alkoxy, for example benzyloxy, or oxo, and can be partly or completely saturated.

Such radicals are, for example, 2- or 3-pyrrolyl, phenylpyrrolyl, for example 4- or 5-phenyl-2-pyrrolyl, 2-furyl, 2-thienyl, 4-imidazolyl, methyl-imidazolyl, for example 1-methyl-2-, -4- or -5-imidazolyl, 1,3-thiazol-2-yl, 2-, 3- or 4-pyridyl, 2-, 3- or 4-pyridyl-N-oxide, 2-pyrazinyl, 2-, 4- or 5-pyrimidinyl, 2-, 3- or 5-indolyl, substituted 2-indolyl, for example 1-methyl-, 5-methyl-, 5-methoxy-, 5-benzyloxy-, 5-chloro- or 4,5-dimethyl-2-indolyl, 1-benzyl-2- or -3-indolyl, 4,5,6,7-tetrahydro-2-indolyl, cyclohepta[b]-5-pyrrolyl, 2-, 3- or 4-quinolyl, 1-, 3- or 4-isoquinolyl, 1-oxo-1,2-dihydro-3-isoquinolyl, 2-quinoxalinyl, 2-benzofuranyl, 2-benzothienyl, 2benzoxazolyl or benzothiazolyl. Partly hydrogenated or completely hydrogenated heterocyclic rings are, for example, dihydropyridinyl, pyrrolidinyl, for example 2-, 3- or 4-N-Methylpyrrolidinyl, piperazinyl, morpholino, thiomorpholino, tetrahydrothienyl, benzodioxolanyl.

Halogen represents fluorine, chlorine, bromine or iodine, in particular fluorine or chlorine.

Naturally occurring and unnatural amino acids, if they are chiral, can be in the D- or L-form. α-Amino acids are preferred. Examples which may be mentioned are (compare Houben-Weyl, Methoden der organischen Chemie, (Methods of organic chemistry), Volume XV/1 and 2, Stuttgart, 1974):

Aad, Abu, χAbu, ABz, 2ABz, εAca, Ach, Acp, Adpd, Ahb, Aib, βAib, AlaβAla, aAla, Alg, All, Ama, Amt, Ape, Apm, Apr, Arg, Asn, Asp, Asu, Aze, Azi, Bai, Bph, Can, Cit, Cys, (Cys)2, Cyta, Daad, Dab, Dadd, Dap, Dapm, Dasu, Djen, Dpa, Dtc, Fel, Gln, Glu, Gly, Guy, hAla, hArg, hCys, hGln, hGlu, His, hIle, hLeu, hLys, hMet, hPhe, hPro, hSer, hThr, hTrp, hTyr, Hyl, Hyp, 3Hyp, Ile, Ise, Iva, Kyn, Lant, Lcn, Leu, Lsg, Lys, βLys, aLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val, Tbg, Npg, Chg, Cha, Thia, 2,2-diphenylaminoacetic acid, 2-(p-tolyl)-2-phenylaminoacetic acid and 2-(p-chlorophenyl)aminoacetic acid.

Amino acid side chains are understood as meaning side chains of naturally occurring or unnatural amino acids.

Azaamino acids are naturally occurring or unnatural amino acids wherein the central unit—CHR— or —CH$_2$— is replaced by —NR— or —NH—.

Possible radicals of an imino acid are, in particular, radicals of heterocyclic compounds from the following group: pyrrolidine-2-carboxylic acid; piperidine-2-carboxylic acid; tetrahydroisoquinoline-3-carboxylic acid; decahydroisoquinoline-3-carboxylic acid; octahydroindole-2-carboxylic acid; decahydroquinoline-2-carboxylic acid; octahydrocyclopenta[b]-pyrrole-2-carboxylic acid; 2-aza-bicyclo-[2.2.2]octane-3-carboxylic acid; 2-azabicyclo[2.2.1]heptane-3-carboxylic acid; 2-azabicyclo[3.1.0]hexane-3-carboxylic acid; 2-azaspiro[4.4]nonane-3-carboxylic acid; 2-azaspiro[4.5]decane-3-carboxylic acid; spiro(bicyclo[2.2.1]-heptane)-2,3-pyrrolidine-5-carboxylic acid; spiro(bicyclo[2.2.2]octane)-2,3-pyrrolidine-5-carboxylic acid; 2-azatricyclo[4.3.0.1$^{6,9}$]-decane-3-carboxylic acid; decahydrocyclohepta[b]pyrrole-2-carboxylic acid; decahydrocycloocta[c]pyrrole-2-carboxylic acid; octahydrocyclopenta[c]pyrrole; octohydroisoindole-1-carboxylic acid; 2,3,3a,4,6a-hexahydrocyclopenta[b]pyrrole-2-carboxylic acid; 2,3,3a,4,5 ,7a-hexahydroindole-2-carboxylic acid; tetrahydrothiazole-4-carboxylic acid; isoxazolidine-3-carboxylic acid; pyrazolidine-3-carboxylic acid; and hydroxyproline-2-carboxylic acid, all of which can optionally be substituted:

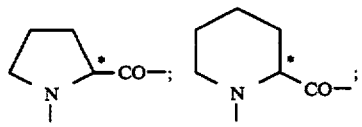

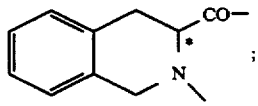

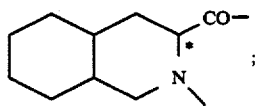

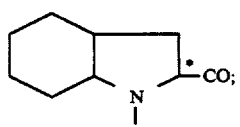

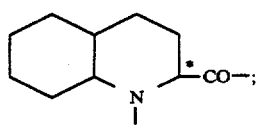

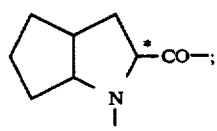

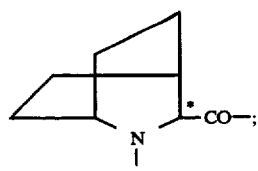

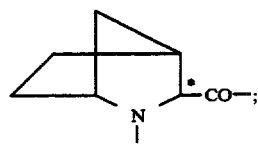

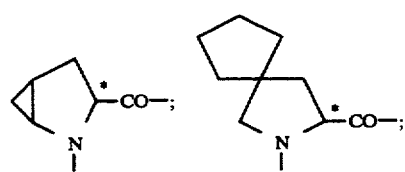

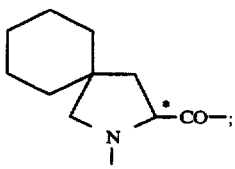
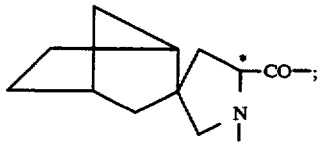
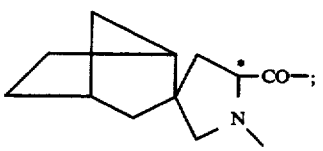
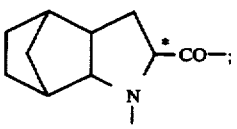
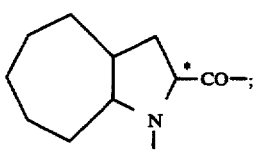
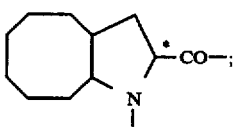
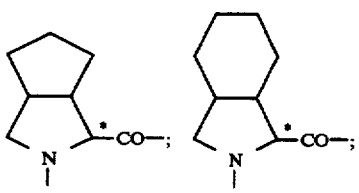
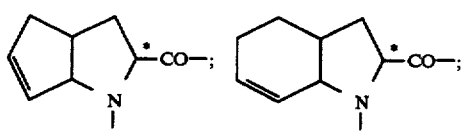
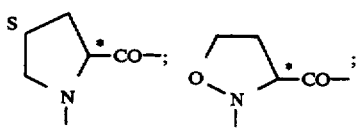

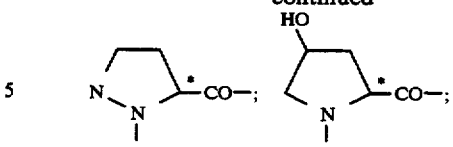

The heterocyclic compounds on which the abovementioned radicals are based are known, for example, from U.S. Pat. No. 4,344,949; U.S. Pat. No. 4,374,847, U.S. Pat. No 4,350,704; EP-A 29,488; EP-A 31,741; EP-A 46,953; EP-A 49,605; EP-A 49,658; EP-A 50,800; EP-A 51,020; EP-A 52,870; EP-A 79,022; EP-A 84,164; EP-A 89,637; EP-A 90,341; EP-A 90,362; EP-A 105,102; EP-A 109,020; EP-A 111,873; EP-A 271,865 and EP-A 344,682.

Dipeptides can contain naturally occurring or unnatural amino acids, imino acids and azaamino acids as structural units. The naturally occurring or unnatural amino acids, imino acids, azaamino acids and dipeptides furthermore can also be in the form of esters or amides, such as, for example, the methyl ester, ethylamide, semicarbazide or $\omega$-amino-$C_4$-$C_8$-alkylamide.

Functional groups of the amino acids, imino acids and dipeptides can be in protected form. Suitable protective groups, such as, for example, urethane protective groups, carboxyl protective groups and side chain protective groups, are described in Hubbuch, Kontakte (Contact catalysts) (Merck) 1979, No. 3, pages 14 to 23, and by Büllesbach, Kontakte (Contact catalysts) (Merck) 1980, No. 1, pages 23 to 35. Groups which may be mentioned in particular are: Aloc, Pyoc, Fmoc, Tcboc, Z, Boc, Ddz, Bpoc, Adoc, Msc, Moc, Z(NO2), Z(Haln), Bobz, Iboc, Adpoc, Mboc, Acm, tert.Butyl, OBzl, ONbzl, OMbzl, Bzl, Mob, Pic and Trt.

Salts of compounds of the formula (I) are to be understood as meaning, in particular, pharmaceutically usable or nontoxic salts.

Such salts are formed, for example, by compounds of the formula (I) which contain acid groups, for example carboxyl, with alkali metals or alkaline earth metals, such as, for example, Na, K, Mg and Ca, and with physiologically tolerated organic amines, such as, for example, triethylamine and tris-(2-hydroxyethyl)amine.

Compounds of the formula (I) which contain basic groups, for example an amino group or a guanidino group, form salts with inorganic acids, such as, for example, hydrochloric acid, sulphuric acid or phosphoric acid, and with organic carboxylic or sulphonic acids, such as, for example, acetic acid, citric acid, benzoic acid, maleic acid, fumaric acid, tartaric acid and p-toluenesulphonic acid.

Preferred compounds of the formula I are those wherein $R^1$ denotes —$CH_2$—$C_6H_4$—C(NH)—$NH_2$ or —$CH_2$—$C_6H_4$—$CH_2$—$NH_2$, $R^2$ denotes H or $CH_3$, Y denotes —$CH_2$—CO— and $R^4$ denotes —CO—NH—$R^5$, wherein NH—$R^5$ represents an α-amino acid radical, preferably a valine or phenylglycine radical.

Compounds of the formula I are prepared by fragment condensation of, for example, compounds of the formula IIIa, IIIb or IIIc with compounds of the formula IV, wherein $R^1$, $R^2$, $R^3$, $R^4$, $X^1$ and m have the abovementioned meanings:

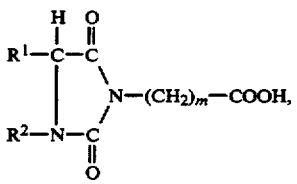
(IIIa)

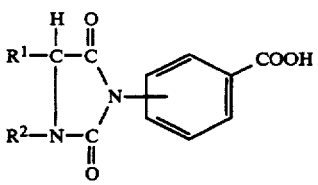
(IIIb)

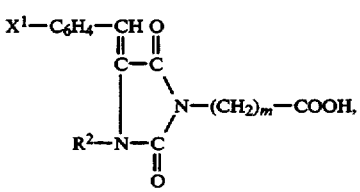
(IIIc)

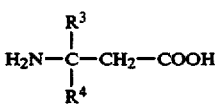
(IV)

Amino groups in $R^1$ and $R^4$ must be protected by reversible protective groups during the condensation. The carboxyl groups in compounds of the formula IV should also be in the form of the benzyl or tert-butyl ester during the condensation. Protection of amino groups is unnecessary if the amino groups to be generated are still in the form of nitro or cyano groups and are formed by hydrogenation only after the coupling. After the coupling, the protective groups present are split off in a suitable manner. $NO_2$ groups (guanidino protection), benzyloxycarbonyl groups and benzyl esters are removed by hydrogenation. The protective groups of the tert-butyl type are cleaved under acid conditions. The 9-fluorenylmethyloxycarbonyl radical is removed by secondary amines. The condensation methods of peptide chemistry are used for coupling e.g. compounds of the formulae IIIa/IIIb/IIIc with compounds of the formula IV.

Hydantoins of the formula Va are formed quite generally by treatment of alkoxycarbonyl or aralkoxycarbonyl peptides of the general formula V with bases (J. S. Fruton and M. Bergmann, J. Biol. Chem. 145 (1942) 253–265; C. A. Dekker, S. P. Taylor, jr. and J. S. Fruton, J. Biol. Chem. 180 (1949) 155–173; M. E. Cox, H. G. Garg, J. Hollowood, J. M. Hugo, P. M. Scopes and G. T. Young, J. Chem. Soc. (1965) 6806–6813; W. Voelter and A. Altenburg, Liebigs Ann. Chem. (1983) 1641–1655; and B. Schwenzer, E. Weber and G. Losse, J. Prakt. Chem. 327 (1985) 479–486):

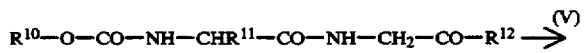
(V)

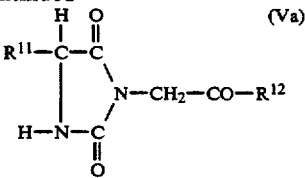
(Va)

wherein $R^{10}$ denotes benzyl or tert-butyl, $R^{11}$ denotes any desired amino acid side chain and $R^{12}$ denotes an amide, an amino acid radical or a peptide radical. In this treatment, however, the N-terminal amino acid is racemised and the hydantoin is hydrolysed into the urea derivative $$HOOC-CH(R^{11})-NH-CO-NH-CH_2-CO-R^{12}$$

(W. Voelter and A. Altenburg, Liebigs Ann. Chem. (1983) 1641–1655).

In contrast, a mild method is cyclisation to give the hydantoin from compounds of the formula V under neutral conditions by treatment with tetrabutylammonium fluoride in tetrahydrofuran under reflux (J. Pless, J. Org. Chem. 39 (1974) 2644–2646).

Another possibility of mild cyclisation is trimethylsilylation of the peptide bond between the N-terminal amino acid and the following glycine with bistrimethylsilyltrifluoroacetamide in acetonitrile (4 hours under reflux) (J. S. Davies, R. K. Merritt and R. C. Treadgold, J. Chem. Soc. Perkin Trans. I (1982) 2939–2947).

In the previous application DE-P 4009506.1 (HOE 90/F 096), it is reported that peptides of formula Vb cyclise to give the hydantoin derivatives even at room temperature, after a relatively long time, or by boiling briefly under reflux with tetrahydrofuran.

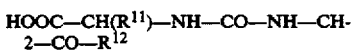

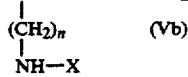

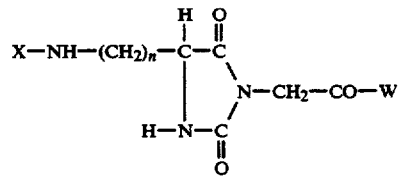

wherein
Z denotes benzyloxycarbonyl,
X=formamidino and
W denotes Otbu, OBzl, or Asp(OtBu)—NH—$R^5$, and possible carboxyl groups are in the form of esters, preferably OtBu or OBzl.

Condensation of amino acids, N-alkylamino acids or, preferably, esters thereof (for example methyl, ethyl, benzyl or tert-butyl esters) of the formula VI with isocyanatoalkanecarboxylic acid esters gives urea derivatives of the formula VII, which cyclise to give the hydantoin derivatives of the formula IIIa by heating in hydrochloric acid, the ester functions being hydrolysed (see DE-P 4009506.1). During the urea synthesis, guanidino groups can be blocked by protective groups (for example $NO_2$ or Mtr). Possible amino groups in the side chain must be in protected form during the urea synthesis (for example as Boc or Z derivatives), or still in the form of NO₂ or the cyano function, which are later reduced to the amino group or, in the case of the cyano group, also converted into the formamidino group, such as, for example,

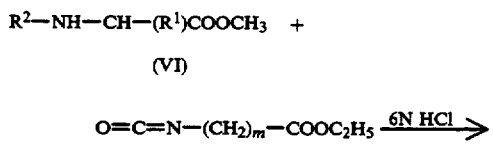

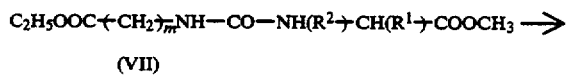

The compounds of the formula IIIb are obtained analogously if, instead of isocyanatoalkanecarboxylic acid esters, the isocyanates of amino-benzoic acid esters are used.

Another possibility of arriving at the hydantoins of the formula IIIa comprises the hydantoins of the formula VIII, which can be alkylated on the imide nitrogen with haloalkanecarboxylic acids or esters thereof (for example alkyl or aralkyl esters) and condensed with suitable aldehydes on the CH₂ function (Gränacher and Landolt, Helv. Chim. Acta 10 (1927) 808). Hydrogenation of the condensation products leads to the starting substances of the formula IIIa according to the invention. If the hydrogenation is carried out only after condensation with compounds of the formula IV, protection of the amino group is saved.

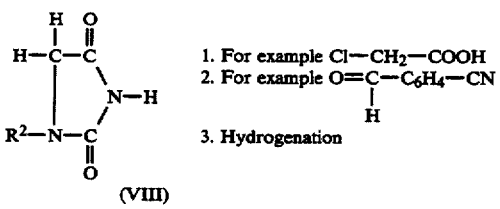

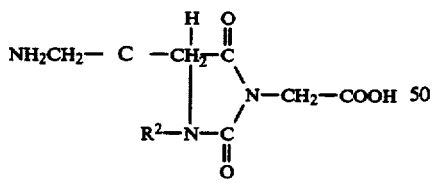

The hydantoin of the formula IIIa where R²=alkyl can also be prepared by the following route: the unsubstituted hydantoin parent substance is first alkylated on the imino nitrogen with haloalkanecarboxylic acid or esters thereof. In order to introduce R¹ the hydantoin thus obtained is subjected to condensation with suitable aldehydes. Thereafter, the second nitrogen is alkylated, if appropriate, with alkyl halides (D. A. Hahn and J. Evans, J. Amer. Chem. Soc. 50 (1928) 806–818) and the double bond and possible nitro groups or cyano groups are hydrogenated in one step, if appropriate only after condensation with compounds of the formula IV. If the radicals of the formula

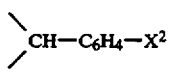

(X²=cyano or acetylamino) have been introduced during the condensation, the radical X² can be converted into the radical X¹ without hydrogenation, to give in this way the compounds of the general formula IIIc.

The guanylation of the amino functions can be carried out using the following reagents:

1. O-Methylisothiourea (S. Weiss and H. Krommer, Chemiker Zeitung 98 (1974) 617–618),
2. S-Methylisothiourea (R. F. Borne, M. L. Forrester and I. W. Waters, J. Med. Chem. 20 (1977) 771–776),
3. Nitro-S-methylisothiourea (L. S. Hafner and R. E. Evans, J. Org. Chem. 24 (1959) 1157),
4. Formamidinesulphonic acid (K. Kim, Y.-T. Lin and H. S. Mosher, Tetrah. Lett. 29 (1988) 3183–3186),
5. 3,5-Dimethyl-1-pyrazolyl-formamidinium nitrate (F. L. Scott, D. G. O'Donovan and J. Reilly, J. Amer. Chem. Soc. 75 (1953) 4053–4054).

The preparation of formamidines from the corresponding cyano compounds can be carried out by adding on methanol or ethanol in an acid anhydrous medium (for example dioxane, ethanol or methanol) and subsequent treatment with ammonia in ethanol or isopropanol (G. Wagner, P. Richter and Ch. Garbs, Pharmazie 29 (1974) 12–55). Another method of preparing formamidines is addition of H₂S onto the cyano group, followed by methylation of the thioamide formed and subsequent reaction with ammonia (East German Patent No. 235,866).

The starting peptides of the formula IV are as a rule built up stepwise from the C-terminal end. The peptide linkages can be achieved using the known coupling methods of peptide chemistry.

The compounds of the general formula I and their physiologically tolerated salts can be administered as medicines by themselves, as mixture with one another or in the form of pharmaceutical formulations which allow enteral or parenteral use and comprise, as the active constituent, an effective dose of at least one compound of the general formula I or of a salt thereof, in addition to customary pharmaceutically innocuous excipients and additives. The formulations usually contain about 0.5 to 90% by weight of the therapeutically active compound.

The medicines can be administered orally, for example in the form of pills, tablets, lacquered tablets, coated tablets, granules, hard and soft gelatine capsules, solutions, syrups, emulsions or suspensions, or as aerosol mixtures. However, administration can also be effected rectally, for example in the form of suppositories, or parenterally, for example in the form of injection solutions or microcapsules, percutaneously, for example in the form of ointments or tinctures, or nasally, for example in the form of nasal sprays.

The pharmaceutical preparations are prepared in a manner which is known per se, pharmaceutically inert inorganic or organic excipients being used. For the preparation of pills, tablets, coated tablets and hard gelatine capsules, it is possible to use, for example, lactose, maize starch or derivatives thereof, talc, stearic acid or salts thereof and the like. Excipients for soft gelatine capsules and suppositories are, for example, fats, waxes, semi-solid and liquid polyols, naturally occurring or solidified oils and the like. Suitable excipients for the preparation of solutions and syrups are, for example, water, sucrose, invert sugar, glucose, polyols, and the like. Suitable excipients for the preparation of injection solutions are water, alcohols, glycerol, polyols, vegetable oils and the like. Suitable excipients for microcapsules or implants are copolymers or glycolic acid and lactic acid.

In addition to the active compounds and excipients, the pharmaceutical preparations can also comprise additives, such as, for example, fillers, extenders, disintegrating agents, binders, lubricants, wetting agents, stabilisers, emulsifiers, preservatives, sweeteners, colouring agents, flavouring or aromatising agents, thickeners, diluents and buffer substances, and furthermore solvents or solubilising agents or agents for achieving a depot effect, as well as salts for modifying the osmotic pressure, coating agents or antioxidants. They can also comprise two or more compounds of the general formula I or their physiologically tolerated salts, and also one or more other therapeutically active substances.

Such other therapeutically active substances are, for example, agents which stimulate blood flow, such as dihydroergocristine, nicergoline, buphenine, nicotinic acid and its esters, pyridylcarbinol, bencyclane, cinnarizine, naftidrofuryl, raubasine and vincamine; positively inotropic compounds, such as digoxin, acetyldigoxin, methldigoxin and lanthanoglycosides; coronary dilators, such as carbocromen, dipyridamole, nifedipine and perhexiline; antianginal compounds, such as isosorbide dinitrate, isosorbide mononitrate, glycerol nitrate, molsidomine and verapamil; and β-blockers, such as propranolol, oxprenolol, atenolol, metoprolol and penbutolol. The compounds moreover can be combined with other nootropic substances, such as e.g. piracetam, or substances having an action on the central nervous system, such as pirlindole, sulpiride, and the like.

The dose can be varied within wide limits, and is to be adjusted to the individual circumstances in each individual case. In general, a daily dose of about 0.1 to 1 mg/kg, preferably 0.3 to 0.5 mg/kg of body weight is appropriate for oral administration to achieve effective results, and for intravenous administration the daily dose is in general about 0.01 to 0.3 mg/kg, preferably 0.05 to 0.1 mg/kg of body weight. The daily dose is usually divided into several, for example 2, 3 or 4, part administrations, especially if relatively large amounts are administered. If appropriate, depending on the individual circumstances, it may be necessary to deviate upwards or downwards from the stated daily dose. Pharmaceutical preparations usually comprise 0.2 to 50 mg, preferably 0.5 to 10 mg of active compound of the formula I or of one of their physiologically tolerated salts per dose.

The compounds according to the invention have the ability to inhibit the cell-cell-adhesion which is based on interactions of glycoproteins containing Arg-Gly-Asp with the so-called integrins. Integrins are transmembrane glycoproteins, or receptors for cell matrix glycoproteins containing Arg-Gly-Asp (E. Ruoslahti and M. D. Pierschbacker, Science 238 (1987) 491–497; and D. R. Phillips, I. F. Charo, L. V. Parise and L. A. Fitzgerald, Blood 71 (1988) 831–843).

The new hydantoin derivatives of the formula I according to the invention inhibit platelet aggregation, formation of metastases and binding of osteoclasts to the bone surfaces.

The hydantoin derivatives of the formula I are therefore used acutely where there is a risk of thrombosis and the risk of reocclusion with cardiac infarction; they are used chronically for the prevention of arteriosclerosis and thrombosis.

Another use is during cancer operations and also prophylactically against cancer. Osteoporosis furthermore can be avoided by inhibition of the binding of osteoclasts to the bone surface.

The compounds are tested above all for their inhibiting action on blood platelet aggregation and the adhesion of fibrinogen to blood platelets.

Gel-filereed blood platelets from human donor blood activated with ADP or thrombin are used.

EXAMPLES

All the products were identified via mass spectra and NMR spectra.

EXAMPLE 1

[5-(S,R )-(4-Formamidino-benzyl )-2,4-dioxoimidazolidin-3-yl ]-acetyl-L-aspartyl-L-valine.

1a. 4-Formamidino-D,L-phenylalanine methyl ester dihydrochloride 11 g (39 mmol) of 4-formamidino-D,L-phenylalanine dihydrochloride are suspended in 110 ml of methanol. 2.9 ml (39 mmol) of thionyl chloride are added dropwise at −10° C., and the mixture is stirred at room temperature for one hour and at 45° C. for 45 minutes.

Since everything has not yet reacted, a further 1 ml of thionyl chloride is added dropwise at −10° C. The mixture is then stirred at 40° C. for 2 hours and left to stand at room temperature over the weekend. Thereafter, it is concentrated in vacuo and the residue is triturated with diethyl ether and filtered off with suction.

Yield: 11.27 g.

To remove impurities, in each case one third of the substance is chromatographed over ®Sephadex LH20 (200×4 cm) in water. The fractions containing the methyl ester are combined and freeze-dried.

Yield: 10.47 g (91%),

Melting point: 166° C.

1b. 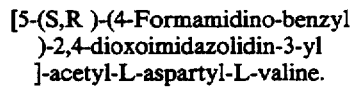
N-[1-Methoxycarbonyl-2-(S,R)-(4-formamidino-phenyl)ethyl]-N'-ethyl-oxycarbonymethyl-urea hydrochloride 1.4 ml (12.74 mmol) of N-ethylmorpholine are added to a solution of 3.73 g (12.74 mmol) of 4-formamidino-D,L-phenylalanine methyl ester dihydrochloride in 28 ml of dimethylformamide at room temperature, and 1.44 ml (12.74 mmol) of ethyl isocyanatoacetate are slowly added dropwise in the course of 15 minutes. The mixture is stirred at room temperature for one hour and concentrated. The oily residue is purified by chromatography as in example 1a and freeze-dried. Yield: 3.82 g (77%) of amorphous substance.

1c. 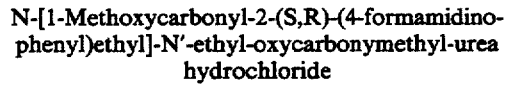
[5-(S,R)-(4-Formamidino-benzyl)-2,4-dioxoimidazoline-3-yl]-acetic acid 3.8 g (9.8 mmol) of N-[1-methoxycarbonyl-2-(S,R)-(4-formamidino-phenyl)ethyl]N'-ethoxycarbonyl-methyl-urea hydrochloride are boiled under reflux in 35 ml of 6N HCl for 30 minutes. The solution is concentrated in vacuo and the residue is dissolved in 250 ml of water. The solution is brought to pH 5 with saturated NaHCO₃ solution and cooled to 0° C. The precipitate is filtered off with suction and dried over P₂O₅ in vacuo. Yield: 2.33 g, melting point: 287° C. (with decomposition). The mother liquor is concentrated, and about 20 ml of water are added. The precipitate which has separated out is filtered off with suction and dried as above.

Yield: 0.22 g.

Total yield: 2.55 g (89%).

1d.
[5-(S,R)-(4-Formamidino-benzyl)-2,4-dioxoimidazolidin-3-yl]-acetyl-Asp(OtBu)-Val-OtBu 340 mg (1.53 mmol) of dicyclohexylcarbodiimide are added to a suspension of 0.5 g of [5-(S,R)-(4-formamidino-benzyl)-2,4-dioxoimidazolidin-3-yl]-acetic acid, 0.583 g of H-Asp(OtBu)-ValOtBu.HCl and 207 mg of HOBt in 5 ml of dimethylformamide at 0° C. The mixture is stirred at 0° C. for one hour and at room temperature for 4 hours. It is then left to stand in a refrigerator over the weekend, the precipitate is filtered off with suction and the filtrate is concentrated. For purification, the substance is chromatographed over silica gel in methylene chloride/methanol/water/glacial acetic acid mixtures, for example 8: 2: 0.2: 0.2.

Yield: 1.03 g of amorphous substance (still contains acetic acid).

1e.
[5-(S,R)-(4-Formamidino-benzyl)-2,4-dioxoimidazolidin-3-yl]-acetyl-L-aspartyl-L-valine 1.03 g of [5-(S,R)-(4-formamidino-benzyl)-2,4-dioxoimidazolidin-3-yl]-acetyl-Asp(OtBu)-Val-OtBu are dissolved in a mixture of 9 ml trifluoroacetic acid, 1 ml of water and 1 ml of dimercaptoethane. After one hour at room temperature, ether is added, and the substance which has precipitated is filtered off with suction. The substance is highly hygroscopic. For purification, the substance is chromatographed over ®Sephadex LH20 in a mixture of glacial acetic acid, n-butanol and water. The fractions containing the pure substance are concentrated. The residue is dissolved in water and freeze-dried.

Yield: 46 1.7 ml, $[\alpha]^{25}_D = -14.9°$ C. (c=1, in acetic acid).

EXAMPLE 2
[1-Methyl-5-(S)-(3-guanidino-propyl)-2,4-dioxoimidazolidin-3-yl]-acetyl-L-aspartyl-L-valine

2a. N-Methyl-L-arginine methyl ester dihydrochloride 6.4 ml of thionyl chloride are added dropwise to a suspension of 15.06 g of N-methylarginine in 50 ml of absolute methanol at −10° C. The mixture is then allowed to come to room temperature, while stirring. Since starting material is still present after a reaction time of 17 hours, a further 9.6 ml of thionyl chloride are added in portions, the mixture is heated at 40° C. for 4 hours, the insoluble material is filtered off with suction and the filtrate is concentrated. The oily residue is dissolved in water, the insoluble material is filtered off and the product is freeze-dried.

Yield: 19.8 g of amorphous substance.

2b.
N-Methyl-N-(1-methoxycarbonyl-2-(S)-(3-guanidino-propyl)ethyl]-N'-ethyloxycarbonylmethyl-urea hydrochloride 1.3 ml of N-ethyimorpholine are added to a suspension of 2.4 g (10 mmol) of N-methyl-L-arginine methyl ester hydrochloride in 10 ml of dimethylformamide, and 1.13 ml of ethyl isocyanatoacetate are immediately added dropwise. After 5–15 minutes, everything dissolves. After about 2 hours, the mixture is concentrated under a high vacuum. The residue is dissolved in water and the insoluble material is filtered off. The filtrate is chromatographed over ®Sephadex LH20 (200×4 cm) using water, and the pure fractions are freeze-dried.

Yield: 2.8 g of amorphous, hygroscopic substance.

2c.
[1-Methyl-5-(S)-(3-guanidino-propyl)-2,4-dioxoimidazolidin-3-yl]-acetic acid hydrochloride The 2.8 g of N-methyl-N-[1-methoxycarbonyl-2-(S)-(3-guanidinopropyl)-ethyl]-N'-ethyloxycarbonyl-methyl-urea hydrochloride obtained above are boiled under reflux in 30 ml of 6N HCl for 30 minutes. Thereafter, the mixture is concentrated under a high vacuum, the residue is dissolved in water and the product is freeze-dried.

Yield: 2.3 g.

For purification, the substance is chromatographed on ®Sephadex LH20 (200×4 cm) using water.

Yield of pure, tacky, amorphous substance: 1.5 g.

2d.
[1-Methyl-5-(S)-(3-guanidino-propyl)-2,4-dioxoimidazolidin-3-yl]-acetyl-Asp(OtBu)-Val-OtBu 0.25 ml of N-ethylmorpholine and 420 mg of dicyclohexylcarbodiimide are added to a solution of 519.5 mg of [1-methyl-5-(S)-(3-guanidino-propyl)-2,4-dioxoimidazolidin-3-yl]-acetic acid hydrochloride, 729 mg of HCl.H-Asp(OtBu)-Val-OtBu and 258 mg of HOBt in 5 ml of dimethylformamide at 0° C. The mixture is stirred at 0° C. for one hour and then for 3 hours, and is allowed to stand at room temperature overnight, and the urea is filtered off with suction on the following day. The filtrate is concentrated. The residue is chromatographed over silica gel using methylene chloride/methanol/glacial acetic acid/water mixtures. The pure fractions are combined and concentrated.

Yield: 600 mg of a very hygroscopic substance.

2e.
[1-Methyl-5-(S)-(3-guanidino-propyl)-2,4-dioxoimidazolidin-3-yl]-acetyl-Asp-Val-OH 600 mg of [1-methyl-5-(S)-(3-guanidino-propyl)-2,4-dioxoimidazolidin-3-yl]-acetyl-Asp(OtBu)-Val-OtBu are dissolved in 6 ml of 90% strength trifluoroacetic acid. The mixture is left to stand at room temperature for one hour, and is then concentrated. The residue is dissolved in water and the product is freeze-dried.

Yield: about 500 mg of a tacky, hygroscopic substance, $[\alpha]^{23}_D = -24 (c=1, \text{in water})$

EXAMPLE 3

[5-(S)-(4-Amino-butyl)-2,4-dioxoimidazolidin-3-yl]-acetyl-Asp-Val-OH

3a.
N-[1-Methoxycarbonyl-2-(4-benzyloxycarboxamido-butyl)-ethyl]-N'-ethyloxycarbonylmethyl-urea 2.6 ml of N-Methylmorpholine are added to a solution of 6.61 g (20 mmol) of H-Lys(Z)-OMe.HCl in 20 ml of dimethylformamide, and 2.26 m of ethyl isocyanatoacetate are im-mediately added dropwise. During this addition, the solution warms up to about 40° C. After about 2 hours, the mixture is concentrated under a high vacuum. The residue is partitioned between ethyl acetate and water. The ethyl acetate phase is extracted by shaking successively with saturated NarCO₃ solution, KHSO₄/K₂SO₄ buffer and water, dried over Na₂SO₄ and concentrated. The residue is triturated with petroleum ether, filtered off with suction and dried.

Yield: 7.44 g,
Melting point: 92°–94° C.

3b.
[5-(S)-(4-Amino-butyl)-2,4-dioxoimidazolidin-3-yl]-acetic acid hydrochloride 7.2 g of N-[1-methoxycarbonyl-2-(4-benzyloxycarboxamidobutyl)-ethyl]-N'-ethoxycarbonylmethyl-urea are heated under reflux in 63 ml of 6N HCl for 30 minutes. Thereafter, the mixture is concentrated under a high vacuum and the residue is dissolved in water. The insoluble material is filtered off and the filtrate is freeze-dried.

Yield: 4.58 g of amorphous hygroscopic substance.

3c.
[5-(S)-4-tert-Butoxycarboxamido-butyl)-2,4-dioxoimidazolidin-3-yl]-acetic acid 2.5 g of di-tert-butyl dicarbonate are added to a solution of 2.36 g of [5-(S)-(4-amino-butyl)-2,4-dioxoimidazolidin-3-yl]-acetic acid hydrochloride and 2.6 g of NaHCO₃ in a mixture of 10 ml of water and 20 ml of dioxane at room temperature. Since hardly any reaction occurs, 0.1N NaOH is added, while monitoring the pH, until a pH of 8 is reached. The mixture is left to stand overnight. The solution is brought to pH 6 with 1N HCl and concentrated. The residue is partitioned between ethyl acetate and KHSO₄/K₂SO₄ buffer. The ethyl acetate phase is dried over Na₂SO₄ and concentrated.

Yield: 2.92 g of an oily substance.

3d.
[5-(S)-(4-tert-Butoxycarboxamido-butyl)-2,4-dioxoimidazolidin-3-yl]-acetyl-Asp(OtBu)-Val-OtBu 0.325 ml of N-ethylmorpholine and 548 mg of dicyclohexylcarbodiimide are added to a solution of 820 mg of [5-(S)-(4-tertbutoxycarboxamido-butyl)-2,4-dioxoimidazolidin-3-yl]-acetic acid, 948 mg of HCl.H-Asp(OtBu)-Val-OtBu and 336 mg of HOBt in 5 ml of dimethylformamide at 0° C. The mixture is stirred at 0° C. for one hour and at room temperature for 3 hours and is left to stand at room temperature overnight, the precipitate is filtered off with suction on the following day, and the filtrate is concentrated. The residue is partitioned between ethyl acetate and water. The ethyl acetate phase is then extracted by shaking successively with saturated NaHCO₃ solution, KHSO₄/K₂SO₄ buffer, saturated NaHCO₃ solution and water, dried over Na₂SO₄ and concentrated.

Yield: 1.82 g of oily substance.

3e.
[5-(S)-(4-Amino-butyl)-2,4-dioxoimidazolidin-3-yl]-acetyl-Asp-Val-OH 1.82 g of [5-(S)-(4-tert-butoxycarboxamido-butyl)-2,4-dioxoimidazolidin-3-yl]-acetyl-Asp(OtBu)-Val-OtBu are dissolved in 18 ml of 90% strength trifluoroacetic acid. The mixture is left to stand at room temperature for one hour and is concentrated in vacuo. The residue is dissolved in water. The insoluble material is filtered off and the filtrate is freeze-dried.

Yield: 1.8 g.

For purification, the substance is chromatographed over ®Sephadex LH20 in an n-butanol/water/acetic acid mixture. The pure fractions are combined and concentrated, the residue is dissolved in water and the product is freeze-dried.

Yield: 0.78 g,
$[\alpha]^{23}_D = -58.8°$ (c=1, in water)

EXAMPLE 4

[5-(S)-(3-Guanidinopropyl)-2,4-dioxoimidazolidin-3-yl]-acetyl-β-alanine

4a.
[5-(S)-(3-Guanidinopropyl)-2,4-dioxoimidazolidin-3-yl]-acetyl-β-alanine-tert-butyl ester 0.88 g of dicyclohexylcarbodiimide are added to a suspension of 0.73 g of HCl.H-β-Ala-OtBu, 1.03 g of [5-(S)-(3-guanidinopropyl)-2,4-dioxoimidazolidin-3-yl]-acetic acid and 0.54 g of HOBt in 30 ml of dimethylformamide at 0° C. The mixture is stirred at 0° C. for one hour and at room temperature for 3 hours. It is then left to stand at room temperature overnight, and the insoluble material is filtered off with suction. The filtrate is concentrated, and the residue is chromatographed over ®Sephadex LH20 in a mixture of glacial acetic acid, butanol and water. The fractions containing the pure substance are concentrated, the residue is dissolved in water and the product is freeze-dried.

Yield: 1.318 g of amorphous substance.

4b.
[5-(S)-(3-Guanidinopropyl)-2,4-dioxoimidazolidin-3-yl]-acetyl-β-alanine 1.3 g of [5-(S)-(3-guanidinopropyl)-2,4-dioxoimidazolidin-3-yl]-acetyl-β-alanine tert-butyl ester are dissolved in 15 ml of 90% strength aqueous trifluoroacetic acid. The mixture is left to stand at room temperature for one hour and concentrated. The residue is dissolved in water and extracted by shaking 3 times with diethyl ether. The aqueous solution is filtered off to remove the insoluble material and freeze-dried.

Yield: 1.16 g,
$[\alpha]^{22}_D = 0.1$ (c=1, in water).

EXAMPLE 5

[5-(S,R)-(4-Formamidino-benzyl)
-2,4-dioxoimidazolidin-3-yl]-acetyl-L-aspartyl-L-
phenylglycine

5a.
[5-(S,R)-(4-Formamidino-benzyl)-2,4-dioxoimidazoli-
din-3-yl]-acetyl-Asp(OtBu)-L-phenylglycine-OtBu Analogously to example 1d, 538 mg of [5-(S,R)-(4-formamidino-benzyl)- 2,4-dioxoimidazolidin-3-yl]-acetic acid and 714 mg of HCl.H-Asp(OtBu)-L-phenylglycine-OtBu reacted with 232 mg HOBt and 375 mg of dicyclohexylcarbodiimide in 5 ml of dimethylformamide.

Yield after purification: 1.01 g of amorphous substance.

5b.
[5-(S,R)-(4-Formamidino-benzyl)-2,4-dioxoimidazoli-
din-3-yl]-acetyl-L-aspartyl-L-phenylglycine 1.01 g of [5-(S,R)-(4-formamidino-benzyl)-2,4-dioxoimidazolidin-3-yl]-acetyl-Asp(OtBu)-L-phenylglycine-OtBu are dissolved in 6 ml of 90% strength trifluoroacetic acid. The mixture is left to stand at room temperature for one hour and is concentrated. The residue is dissolved in water, the insoluble material is filtered off and the product is freeze-dried.

Yield: 832 mg,
$[\alpha]^{28}_D = +9.7°$ (c=1, in water).

EXAMPLE 6

[5-(S,R)-(4-Formamidino-benzyl)
-2,4-dioxoimidazolidin-3-yl]-acetyl-β-alanine

6a.
[5-(S,R)-(4-Formamidino-benzyl)-2,4-dioxoimidazoli-
din-3-yl]-acetyl-β-alanine-OtBu Analogously to example 1d, 500 mg of [5-(S,R)-(4-formamidino-benzyl)-2,4-dioxoimidazolidin-3-yl]-acetic acid and 312 mg of β-alanine-OtBu.HCl can be reacted with 232 mg HOBt and 375 mg of dicyclohexylcarbodiimide.

Yield after purification: 500 mg

6b.
[5-(S,R)-(4-Formamidino-benzyl)-2,4-dioxoimidazoli-
din-3-yl]-acetyl-β-alanine 500 mg of [5-(S,R)-(4-formamidino-benzyl)-2,4-dioxoimidazolidin-3-yl]-acetyl-β-alanine-OtBu are dissolved in 5 ml of 90% strength trifluoroacetic acid. The mixture is left to stand at room temperature for one hour and is concentrated. The residue is dissolved in water, the insoluble material is filtered off and the filtrate is freeze-dried.

Yield: 388 mg
$[\alpha]^{28}_D = 0°$ (c=1, in water).

EXAMPLE 7

(5-(S)-(-4-Aminobenzyl)-2,4-dioxoimidazolidine
-3-yl)-acetyl-L-aspartyl-L-valine

7a.
N-(1-Methoxycarbonyl-2(S)-(4-nitrophenyl)-ethyl)-N'-
ethoxycarbonylmethyl-urea 6.1 ml (48 mmol) of N-ethylmorpholine are added dropwise to 12.5 g (48 mmol) of H-Phe-(4-NO2)-OMe.HCl and 6.2 g (48 mmol) of ethyl isocyanatoacetate in 100 ml of dimethylformamide at room temperature. The mixture is stirred for 4 hours, the product which has precipitated is filtered off with suction, the filtrate is precipitated with water, the product which has further precipitated is filtered off with suction, and the final product is dried over phosphorus pentoxide.

Yield: 16.2 g (95%)
Melting point: 180°–181° C.

7b.
(5-(S)-(4-Nitrobenzyl)-2,4-dioxoimidazolidin-3-yl)-
acetic acid 3.45 g (9.8 mmol) of N-(1-methoxycarbonyl-2(S)-(4-nitrophenyl)-ethyl-N'ethoxycarbonylmethyl-urea are heated under reflux with 40 ml of 6N HCl and 20 ml of acetic acid for 30 minutes. The product which has crystallised out on cooling is filtered off with suction and dried.

Yield: 2.5 g (87%)
Melting point: 211°–213° C.

7c.
(5-(S)-(4-Nitrobenzyl)-2,4-dioxoimidazolidin-3-yl)-acet-
yl-Asp(OtBu)-Val-OtBu 115 mg (0.55 mmol) of dicyclohexylcarbodiimide are added to a suspension of 150 mg (0.5 mmol) of (5-(S)-(4-nitrobenzyl)-2,4-dioxoimidazolidin-3-yl)-acetic acid, 190 mg (0.5 mmol) of H-Asp-(OtBu)-Val-OtBu.HCl, 68 mg (0.5 mmol) of HOBt and 71 µl (0.5 mmol) of N-ethylmorpholine in 5 ml of dimethylformamide at 0° C. The mixture is stirred at 0° C. for one hour and at room temperature for 4 hours, the precipitate is filtered off with suction, the filtrate is concentrated, the residue is dissolved in methylene chloride, and the solution is extracted with sodium bicarbonate solution and with potassium hydrogen sulphate solution. The organic phase is concentrated.

Yield: 300 mg (also contains a little dicyclohexylurea)
Melting point: 90° C.

7d.
(5-(S)-(4-Nitrobenzyl)-2,4-dioxoimidazolidin-3-yl)-acet-
yl-L-aspartyl-L-valine 4.5 ml of trifluoroacetic acid and 0.5 ml of water are added to 270 mg (0.436 mmol) of 5-(S)-(4-nitrobenzyl)-2,4-dioxoimidazolidin-3-yl)-acetyl-Asp(OtBu)-Val-OtBu. After one hour, the mixture is concentrated and the product is freeze-dried.

Yield: 220 mg.

7e.
(5-(S)-(4-Aminobenzyl)-2,4-dioxoimidazolidin-3-yl)-
acetyl-L-aspartyl-L-valine 220 mg (0.43 mmol) of (5-(S)-(4-nitrobenzyl)-2,4-dioxoimidazolidin-3-yl)-acetyl-L-aspartyl-L-valine are dissolved in 50 ml of methanol. After addition of 10 mg of 10% strength Pd-on-charcoal, the mixture is hydrogenated at room temperature for 3 hours, the catalyst is filtered off, the filtrate is concentrated and the product is freeze-dried.

Yield: 150 mg

To remove impurities, the product is chromatographed over ®Sephadex LH20 in butanol/acetic acid/water.

Yield: 75 mg
Melting point: 175°–178° C.

EXAMPLE 8

(5-(S)-(4-Guanidinobenzyl)-2,4-dioxoimidazolidin-3-yl)-acetyl-L-aspartyl-L-valine

8a.
N-(1-Methoxycarbonyl-2-(S)-(4-aminophenyl)-ethyl-N'-ethoxycarbonylmethyl-urea 7.1 g (20 mmol) of N-(1-methoxycarbonyl-2-(S)-(4-nitrophenyl)-ethyl)-N'-ethoxycarbonylmethyl-urea are dissolved in 80 ml of dimethylformamide and, after addition of 100 mg of 10% strength Pd-on-charcoal, are hydrogenated at room temperature for hours, the catalyst is filtered off and the filtrate is concentrated.

Yield: 7.7 g (still contains dimethylformamide)

8b.
(5-(S)-(4-Aminobenzyl)-2,4-dioxoimidazolidin-3-yl)-acetic acid hydrochloride 1 g (3.1 mmol) of N-(1-methoxycarbonyl-2-(S)-(4-aminophenyl)-ethyl-N'-ethoxycarbonylmethyl-urea are heated under reflux in 10 ml of 6N HCl for 30 minutes. After concentration, 1 g of a hygroscopic resin is obtained.

Alternatively, the free base of 8b. can be prepared as follows:

1.1 g (3.75 mmol) of (5-(S)-(4-nitrobenzyl)-2,4-dioxoimidazolidin-3-yl)-acetic acid are dissolved in 50 ml of methanol. After addition of 50 mg of 10% strength Pd-on-charcoal, hydrogenation is carried out at room temperature for 3 hours, the catalyst is filtered off, the filtrate is concentrated and the product is freeze-dried.

Yield: 0.9 g (91%)
Melting point: 130° C.

8c.
(5-(S)-(4-Nitroguanidinobenzyl)-2,4-dioxoimidazolidin-3-yl)-acetic acid 680 mg (5 mmol) of nitor-S-methyl-isothiourea and 900 mg (3.4 mmol) of (5-(S)-(4-aminobenzyl)-2,4-dioxoimidazolidin-3-yl)-acetic acid are stirred in 35 ml of 0.1N sodium hydroxide solution at 80° C. for 5.5 hours. After cooling, the mixture is extracted with methylene chloride and ethyl acetate, and the aqueous phase is acidified to pH 2-3 with hydrochloric acid and concentrated. The residue is stirred with a little water and filtered off with suction.

Yield: 430 mg (36%), further product is obtainable from the filtrate

8d.
(5-(S)-(4-Nitroguanidinobenzyl)-2,4-dioxoimidazolidin-3-yl)-acetyl-Asp(OtBu)-Val-OtBu 45 mg (0.22 mmol) of dicyclohexylcarbodiimide are added to a suspension of 70 mg (0.2 mmol) of (5-(S)-(4-nitroguanidinobenzyl)-2,4-dioxoimidazolidin-3-yl)-acetic acid, 76 mg (0.2 mmol) of H-Asp-(OtBu)-Val-OtBu.HCl, 27 mg (0.2 mmol) of HOBt and 35 µl (0.27 mmol) of N-ethylmorpholine in 3 ml of dimethylformamide at 0° C. The mixture is stirred at 0° C. for one hour and at room temperature for 3 hours, the precipitate is filtered off with suction, the filtrate is concentrated, the residue is dissolved in methylene chloride and the solution is extracted with sodium bicarbonate solution and with potassium hydrogen sulphate solution. The organic phase is concentrated and the product is freeze-dried.

Yield: 145 mg (also contains a little dicyclohexylurea)

8e.
(5-(S)-(4-Nitroguanidinobenzyl)-2,4-dioxoimidazolidin-3-yl)-acetyl-L-aspartyl-L-valine 4.5 ml of trifluoroacetic acid and 0.5 ml of water are added to 130 mg of (5-(S)-(4-nitroguanidinobenzyl)-2,4-dioxoimidazolidin-3-yl)-acetyl-Asp(OtBu)-Val-OtBu. After one hour, the mixture is concentrated and the product is freeze-dried.

Yield: 140 mg (also contains a little dicyclohexylurea).

8f.
(5-(S)-(4-Guanidinobenzyl)-2,4-dioxoimidazolidin-3-yl)-acetyl-L-aspartyl-L-valine 120 mg (0.21 mmol) of 5-(S)-(4-nitroguanidinobenzyl)-2,4-dioxoimidazolidin-3-yl)-acetyl-L-aspartyl-L-valine are dissolved in 50 ml of methanol. After addition of 20 mg of 10% strength Pd-on-charcoal, hydrogenation is carried out at room temperature for 4 hours, the catalyst is filtered off, the filtrate is concentrated and the product is freeze-dried.

Yield: 50 mg (45%), (hygroscopic substance)

EXAMPLE 9

(5-(4-Aminomethylbenzyl)-1-methyl-2,4-dioxoimidazolidin-3-yl)-acetyl-L-aspartyl-L-valine

9a.
N-Methyl-N-ethoxycarbonylmethyl-N'-ethoxycarbonylmethyl-urea 6.4 ml (50 mmol) of N-ethylmorpholine are added dropwise to 7.7 g (50 mmol) of safcosine ethyl ester.HCl and 6.5 g (50 mmol) of ethyl isocyanatoacetate in 30 ml dimethylformamide at room temperature. The mixture is stirred for 4 hours, the N-ethylmorpholine.HCl which has precipitated is filtered off with suction and the filtrate is concentrated. The resulting oil crystallises on standing, and the solid is stirred with tert-butyl methyl ether and filtered off with suction.

Yield: 11.9 g (97%).
Melting point: 82°–85° C.

9b. (1-Methyl-2,4-dioxoimidazolidin-3-yl)-acetic acid 10.5 g (42.6 mmol) of N-methyl-N-ethoxycarbonylmethyl-N-ethoxycarbonylmethyl-urea are heated under reflux in 150 ml of 6N HCl for 60 minutes. After concentration and freeze-drying, 7.4 g of product are obtained.

9c.
(5-(4-Cyanobenzylidene)-1-methyl-2,4-dioxoimidazolidin-3-yl)-acetic acid 2.6 g (15 mmol) of (1-methyl-2,4-dioxoimidazolidin-3-yl)-acetic acid, 2.9 g (22 mmol) of 4-cyanobenzaldehyde, 1.8 g (22 mmol) of sodium acetate and 2.1 ml (22 mmol) of acetic anhydride are heated under reflux in 25 ml of acetic acid for 6 hours. After cooling, the mixture is poured onto ice and extracted with ethyl acetate. The ethyl acetate phase is extracted with sodium bicarbonate solution and the aqueous phase is acidified. The product which has precipitated is filtered off with suction and dried.

Yield: 0.62 g
Melting point: 240°–245° C.
Further product can be obtained from the filtrate.

9d.
(5-(4-Cyanobenzylidene)-1-methyl-2,4-dioxoimidazolidin-3-yl)-acetyl-Asp(OtBu)-Val-OtBu 120 mg (0.58 mmol) of dicyclohexylcarbodiimide are added to 150 mg (0.53 mmol) of 5-(4-cyanobenzylidene)-1-methyl-2,4-dioxoimidazolidin-3-yl)-acetic acid, 200 mg (0.53 mmol) of H-Asp-(OtBu)-Val-OtBu-HCl, 66 mg (0.49 mmol) of HOBt and 110 μl (0.86 mmol) of N-ethylmorpholine in 10 ml of dimethylformamide at 0° C. The mixture is stirred at 0° C. for one hour and at room temperature for 5.5 hours, the precipitate is filtered off with suction, the filtrate is concentrated, the residue is dissolved in methylene chloride and the solution is extracted with sodium bicarbonate solution and with potassium hydrogen sulphate solution. The organic phase is concentrated and the product is freeze-dried.

Yield: 360 mg (also contains a little dicyclohexylurea)

9e.
5-(4-Cyanobenzylidene)-1-methyl-2,4-dioxoimidazolidin-3-yl)-acetyl-L-aspartyl-L-valine 4.5 ml of trifluoroacetic acid and 0.5 ml of water are added to 360 mg of (5-(4-cyanobenzylidene)-1-methyl-2,4-dioxoimidazolidin-3-yl)-acetyl-Asp(OtBu)-Val-OtBu. After one hour, the mixture is concentrated and the product is freeze-dried.

Yield: 340 mg (also contains a little dicyclohexylurea).

9f.
(5-(4-Aminomethylbenzyl)-1-methyl-2,4-dioxoimidazolidin-3-yl)-acetyl-L-aspartyl-L-valine 150 mg of (5-(4-cyanobenzylidene)-1-methyl-2,4-dioxoimidazolidin-3-yl)-acetyl-L-aspartyl-L-valine are dissolved in 40 ml of methanol. After addition of 50 mg of 10% strength Pd-on-charcoal, hydrogenation is carried out at room temperature for 12 hours, the catalyst is filtered off, the filtrate is concentrated and the product is freeze-dried.

EXAMPLE 10

(5-(4-Aminomethylbenzyl)-2,4-dioxoimidazolidin-3-yl)-acetyl-L-aspartyl-L-valine

10a. (5-(4-Cyanobenzylidene)-2,4-dioxoimidazolidine 36.7 g (0.28 mol) of 4-cyanobenzaldehyde, 10 g (0.1 mol) of hydantoin, 21.6 g (0.263 mol) of sodium acetate and 28.6 ml (0.3 mol) of acetic anhydride are heated under reflux in 85 ml of acetic acid for 4 hours. After cooling, the mixture is poured onto ice and extracted with methylene chloride. The methylene chloride phase is concentrated, and the residue is stirred with methanol and filtered off with suction.

Yield: 9.9 g (47%)
Melting point: 310°-315° C.

10b. Benzyl (5-(4-Cyanobenzylidene)-2,4-dioxoimidazolidin-3-yl)-acetate 6.4 g (0.03 mol) of (5-(4-cyanobenzylidene)-2,4-dioxoimidazolidine and 3.5 g (0.031 mol) of potassium tert-butylate are dissolved in 30 ml of dimethylformamide. After addition of 7.1 g (0.031 mol) of benzyl bromoacetate, the mixture is stirred at room temperature for 7 hours, heated briefly to 100° C. and concentrated. Water is added to the residue, and the mixture is extracted with ethyl acetate. The product crystallises out of the ethyl acetate phase, or can be precipitated by addition of heptane.

Yield: 7.5 g (69%)

10c.
(5-(4-Cyanobenzylidene)-2,4-dioxoimidazolidin-3-yl)-acetic acid 0.4 g (1.1 mmol) of benzyl (5-(4-cyanobenzylidene)-2,4-dioxoimidazolidin-3-yl)-acetate are heated under reflux with 5 ml of 6N HCl and 5 ml of acetic acid for 30 minutes, the mixture is filtered hot and the filtrate is cooled. The product which has precipitated is filtered off with suction, washed with water and dried.

Yield: 150 mg (50%)

Alternatively, this compound can be prepared as follows:

5 g (32 mmol) of hydantoin-3-acetic acid, 6.3 g (48 mmol) of 4-cyanobenzaldehyde, 15 g (183 mmol) of sodium acetate and 10 ml (106 mmol) of acetic anhydride are heated under reflux in 30 ml of acetic acid for 1.5 hours. After cooling, the mixture is poured onto ice and acidified to pH 3 with concentrated HCl, and the product is filtered off with suction and recrystallised from acetic acid.

Yield: 2 g

Further product can be obtained from the filtrate.

10d.
(5-(4-Cyanobenzylidene)-2,4-dioxoimidazolidin-3-yl)-acetyl-Asp(OtBu)-Val-OtBu 210 mg (1 mmol) of dicyclohexylcarbodiimide are added to 244 g (0.9 mmol) of (5-(4-cyanobenzylidene-2,4-dioxoimidazolidin-3-yl)-acetic acid, 350 mg (0.9 mmol) of H-Asp-(OtBu)-ValOtBu.HCl, 122 mg (0.9 mmol) of HOBt and 104 mg (0.9 mmol) of N-ethylmorpholine in 50 ml of dimethylformamide at 0° C. The mixture is stirred at 0° C. for one hour and at room temperature for 5 hours, the precipitate is filtered off with suction, the filtrate is concentrated, the residue is dissolved in methylene chloride and the solution is extracted with sodium bicarbonate solution and with potassium hydrogen sulphate solution. The organic phase is concentrated and the product is freeze-dried.

Yield: 640 mg (also contains a little dicyclohexylurea)

10e.
(5-(4-Cyanobenzylidene)-2,4-dioxoimidazolidin-3-yl)-acetyl-L-aspartyl-L-valine 570 mg (0.95 mmol) of (5-(4-cyanobenzylidene)-2,4-dioxoimidazolidin-3-yl)-acetyl-Asp(OtBu)-Val-OtBu are left to stand with 5.4 ml of trifluoroacetic acid and 0.6 ml of water at room temperature for one hour, and the mixture is concentrated.

Yield: 500 mg (also contains a little dicyclohexylurea)

10f.
(5-(4-Aminomethylbenzyl)-2,4-dioxoimidazolidin-3-yl)-acetyl-L-aspartyl-L-valine 400 mg of (5-(4-cyanobenzylidene)-2,4-dioxoimidazolidin-3-yl)-acetyl-L-aspartyl-L-valine are dissolved in 60 ml of methanol. After addition of 50 mg of 10% strength Pd-on-charcoal, hydrogenation is carried out at room temperature for 12 hours, the catalyst is filtered off, the filtrate is concentrated and the product is freeze-dried.

EXAMPLE 11

3-(5-(S)-(3-Guanidinopropyl)-2,4-dioxoimidazolidin-3-yl)benzoyl-L-aspartyl-L-valine

11a.
N-(1-Methoxycarbonyl-(4-(S)-nitroguanidino)-butyl)-N'-(3-ethoxycarbonyl-phenyl-urea 5 g (26 mmol) of ethyl 3-isocyanatobenzoate and 7 g (26 mmol) of H-Arg(NO2)-OMe.HCl are dissolved in 50 ml of dimethylformamide. 5 ml (48 mmol) of N-ethylmorpholine are added dropwise at room temperature, the mixture is stirred at 50° C. for 8 hours and concentrated, the residue is dissolved in methylene chloride and the solution is extracted with dilute hydrochloric acid. The organic phase is concentrated and the residue is chromatographed over a silica gel column in methylene chloride/methanol=98:2 to 90:10.

Yield: 4.1 g (37%) and 3.1 g of the corresponding acid

11b.
3-(5-(S)-(3-Nitroguanidinopropyl)-2,4-dioxoimidazolidin-3-yl)-benzoic acid 2 g (4.7 mmol) of N-(1-methoxycarbonyl-(4-(S)-nitroguanidino)-butyl-N'-(3-ethoxycarbonylphenyl)-urea are boiled under reflux with 40 ml of 6N HCl for 30 minutes. After cooling, the crystals which have precipitated are filtered off with suction and dried.

Yield: 1.8 g (95%)
Melting point: 105°-110° C.

11c.
3-(5-(S)-(3-Nitroguanidinopropyl)-2,4-dioxoimidazolidin-3-yl)-benzoyl-Asp(OtBu)-Val-OtBu 210 mg (1.01 mmol) of dicyclohexylcarbodiimide are added to a suspension of 335 mg (0.92 mmol) of 3-(5-(S)-(3-nitroguanidino-propyl)-2,4-dioxoimidazolidin-3-yl)benzoic acid, 350 mg (0.92 mmol) of H-Asp-(OtBu)-Val-OtBu.HCl, 130 mg (0.92 mmol) of HOBt and 110 mg (0.92 mmol) of N-ethylmorpholine in 10 ml of dimethyformamide at 0° C. The mixture is stirred at 0° C. for one hour and at room temperature for 4 hours, the precipitate is filtered off with suction, the filtrate is concentrated, the residue is dissolved in methylene chloride and the solution is extracted with sodium bicarbonate solution and with potassium hydrogen sulphate solution. The organic phase is concentrated.

Yield: 400 mg (63%)

11d.
3-(5-(S)-(3-Nitroguanidinopropyl)-2,4-dioxoimidazolidin-3-yl)-benzoyl-L-aspartyl-L-valine 400 mg (0.58 mmol) of 3-(5-(S)-(3-nitroguanidinopropyl)-2,4-dioxoimidazolidin-3-yl)-benzoyl-Asp(OtBu)-Val-OtBu are left to stand with 4.5 ml of trifluoroacetic acid and 0.5 ml of water at room temperature for one hour, and the mixture is concentrated.

Yield: 290 mg (94%).

11e.
3-(5-(S)-(3-Guanidinopropyl)-2,4-dioxoimidazolidin-3-yl)aspartyl-L-valine 250 mg (0.36 mmol) of 3-(5-(S)-(3-nitroguanidinopropyl)-2,4-dioxoimidazolidin-3-yl)-benzoyl-acetyl-L-aspartyl-L-valine are dissolved in 30 ml of methanol. After addition of 20 mg of 10% strength Pd-on-charcoal, hydrogenation is carried out at room temperature for 4 hours, the catalyst is filtered off, the filtrate is concentrated and the product is freeze-dried.

$[\alpha]^{25}_D = -20.8°$ (c=0.53, water)

EXAMPLE 12

(5-(R,S)-(4-Formamidinobenzyl)-2,4-dioxo-imidazolidin-3-yl)-acetyl-L-aspartyl-L-isoleucine This compound was prepared by a method analogous to that described in example 1.

$[\alpha]^{23}_D = -31.6°$ (c=1, water)

EXAMPLE 13

(5-(R,S)-(4-Formamidinobenzyl)-2,4-dioxo-imidazolidin-3-yl)-acetyl-L-aspartyl-L-lysine This compound was prepared by a method analogous to that described in example 1.

$[\alpha]^{23}_D - 17.4°$ (c=1, water)

EXAMPLE 14

(5-(R,S)-(4-Formamidinobenzyl)-2,4-dioxo-imidazolidin-3-yl)-acetyl-L-aspartyl-L-phenylalanine This compound was prepared by a method analogous to that described in example 1.

$[\alpha]^{23}_D - 18.9°$ C. (c=1, water)

EXAMPLE 15

(5-(4-Aminomethylbenzylidene)-2,4-dioxo-imidazolidin-3-yl)-acetyl-L-aspartyl-L-phenylglycine 28 mg (0.24 mmol) of N-ethylmorpholine and 54 mg (0.26 mmol) of dicyclohexylcarbodiimide are added to 90 mg (0.24 mmol) of 5-(4-tert-butoxycarbonylaminomethylbenzylidene-2,4-dioxo-imidazolidin-3-yl)-acetic acid, 103 mg (0.24 mmol) of H-Asp(OtBu)-phenylglycine-OtBu hydrochloride, and 32 mg (0.24 mmol) of hydroxybenzotriazole in 15 ml of dimethylformamide at 0° C. The mixture is stirred at 0° C. for one hour and then at room temperature overnight. The reaction mixture is concentrated in vacuo, the residue is taken up in ethyl acetate, and the organic phase is extracted with sodium bicarbonate solution, potassium bicarbonate solution and water, dried over magnesium sulphate and concentrated. The resulting product (200 mg) is stirred with 5 ml of 95% strength trifluoroacetic acid at room temperature for one hour, and the mixture is concentrated in vacuo. For purification, the crude product is chromatographed on Sephadex LH20 with a homogeneous mixture of butanol/glacial acetic acid/water.

Yield: 100 mg
Melting point: 48° C.

EXAMPLE 16

(5-(R,S)-(4-Formamidinobenzyl)-2,4-dioxo-imidazolidin-3-yl)-acetyl-L-aspartyl-L-threonine This compound was prepared by a method analogous to that described in example 1.

$[\alpha]^{23}_D = -20.1°$ (c=1, water)

EXAMPLE 17

(5-(R,S)-(4-Formamidinobenzyl)-2,4-dioxo-imidazolidin-3-yl)-acetyl-L-aspartyl-L-phenylglycine) 1-hexadecyl ester This compound was prepared by a method analogous to that described in example 1.

FAB-MS 763.5 (M+H)+

EXAMPLE 18

(5-(S)-(4-Guanidinobenzyl)-2,4-dioxo-imidazolidin-3-yl)-acetyl-L-aspartyl-L-phenylglycine This compound was prepared by a method analogous to that described in example 1.
Melting point: 48° C.
$[\alpha]^{20}_D = +14°$ (c=0.5, water)

EXAMPLE 19

(5-(4-Aminomethylbenzyl)-2,4-dioxo-imidazolidin-3-yl)-acetyl-L-aspartyl-L-phenyglycine 53 mg (0.1 mmol) of (5-(4-aminomethylbenzylidene)-2,4-dioxo-imidazolidin-3-yl)-acetyl-L-phenylglycine are dissolved in 20 ml of methanol and 5 ml of dimethylformamide and, after addition of 19 g of 10% strength palladium-on-charcoal, are hydrogenated at room temperature. The catalyst is filtered off, the filtrate is concentrated and the residue is freeze-dried.
FAB-MS 526.2 (M+H)+

EXAMPLE 20

(5-(R,S)-(4-Formamidinobenzyl)-2,4-dioxo-imidazolidin-3-yl)-acetyl-L-aspartyl-(N-methyl)-L-phenylglycine This compound was prepared by a method analogous to that described in example 1.
$[\alpha]^{23}_D = -26.3°$ (c=1, water)

EXAMPLE 21

(5-(R,S)-(4-Formamidinobenzyl)-2,4-dioxo-imidazolidin-3-yl)-acetyl-L-aspartyl-L-valine benzyl ester This compound was prepared by a method analogous to that described in example 1.
$[\alpha]^{23}_D = -37°$ (c=1, methanol)

EXAMPLE 22

(5-(R,S)-(4-Formamidinobenzyl)-2,4-dioxo-imidazolidin-3-yl)-acetyl-L-aspartyl-L-tryptophan This compound was prepared by a method analogous to that described in example 1.
$[\alpha]^{24}_D = -7.9°$ (c=1, 80% strength acetic acid)

EXAMPLE 23

(5-(S)-(4-Aminobutyl)-2,4-dioxo-imidazolidin-3-yl)-acetyl-L-aspartyl-L-valine

This compound was prepared by a method analogous to that described in example 1.
$[\alpha]^{24}_D = -58.8°$ C. (c=1, water)

EXAMPLE 24

(5-(4-Aminobenzylidene)-2,4-dioxo-imidazolidin-3-yl)-acetyl-L-aspartyl-L-valine

This compound was prepared by a method analogous to that described in example 15.
Melting point: 160° C.
$[\alpha]^{25}_D = 39.3°$ (c=0.28, water:acetic acid=95:5)

EXAMPLE 25

(5-(4-Formamidinobenzylidene)-2,4-dioxo-imidazolidin-3-yl)-acetyl-L-aspartyl-L-phenylglycine This compound was prepared by a method analogous to that described in example 15.

EXAMPLE 26

(5-(R,S)-(4-Formamidinobenzyl)-2,4-dioxo-imidazolidin-3-yl)-acetyl-L-aspartyl-L-phenylglycine This compound was prepared by a method analogous to that described in example 1.

EXAMPLE 27

(5-(4-Formamidinobenzylidene)-1-methyl-2,4-dioxo-imidazolidin-3-yl)-acetyl-L-aspartyl-L-phenylglycine This compound was prepared by a method analogous to that described in example 15.

EXAMPLE 28

(5-(R,S)-(4-Formamidinobenzyl)-1-methyl-2,4-dioxo-imidazolidin-3-yl)-acetyl-L-aspartyl-L-phenylglycine This compound was prepared by a method analogous to that described in example 1.

EXAMPLE 29

(5-(3-Aminomethylbenzyl)-2,4-dioxo-imidazolidin-3-yl)-acetyl-L-aspartyl-L-phenylglycine This compound was prepared by a method analogous to that described in example 15.

EXAMPLE 30

3-(5-(S)-(3-Aminopropyl)-2,4-dioxo-imidazolidin-3-yl)-benzoyl-L-aspartyl-L-phenylglycine This compound was prepared by a method analogous to that described in example 1.

EXAMPLE 31

(5-(R,S)-(4-Formamidinobenzyl)-2,4-dioxo-imidazolidin-3-yl)-acetyl-L-aspartyl-L-(1-hexydecanoyl)-lysine This compound was prepared by a method analogous to that described in example 1.

EXAMPLE 32

(5-(S)-(4-Aminobutyl)-2,4-dioxo-imidazolidin-3-yl)-propionyl-L-aspartyl-L-valine This compound was prepared by a method analogous to that described in example 1.
$[\alpha]^{23}_D = 47.5°$ (c=1, water)

EXAMPLE 33

(5-(S)-(4-Aminobutyl)-2,4-dioxo-imidazolidin-3-yl)-propionyl-L-aspartyl-L-phenylglycine This compound was prepared by a method analogous to that described in example 1.
$[\alpha]^{23}_D = +10.2°$ (c=1, water)

PHARMACOLOGICAL DATA

A) Inhibition of bonding of fibrinogen to its receptor (glycoprotein IIb/IIIa) on intact, gel-filtered human platelets by the compounds according to the invention is tested. The $K_i$ value of the inhibition of the bonding of $^{125}$I-fibrinogen after stimulation with ADP (10 μM) is stated.

Literature: J. S. Bennett and G. Vilaire, J. Clin. Invest. 64 (1979), 1393–1401

E. Kornecki et al., J. Biol. Chem. 256 (1981), 5695–5701

G. A, Marguerie et al., J. Biol. Chem. 254 (1979), 5357–5363

G. A, Marguerie et al., J. Biol. Chem. 255 (1980), 154–161

| Example | $K_1$ (μm), ADP stimulated |
|---|---|
| 1 | 0.031 |
| 2 | 0.4 |
| 5 | 0.022 |
| 6 | 1.91 |
| 7 | 2.43 |
| 8 | 0.71 |
| 11 | 1.87 |
| 12 | 0.042 |
| 13 | 0.042 |
| 14 | 0.27 |
| 15 | 0.28 |
| 16 | 0.12 |
| 20 | 1.59 |
| 21 | 0.24 |
| 22 | 0.14 |
| 32 | 2.71 |

B) As a functional test, the inhibition of aggregation of gel-filtered human platelets by the compounds according to the invention after ADP or thrombin stimulation is measured. The $IC_{50}$ value of the inhibition is stated.

Literature: G. A. Marguerie et al., J. Biol. Chem. 254 (1979), 5357–5363

| | $IC_{50}$ (μM), | |
|---|---|---|
| Example | ADP-stimulated | Thrombin-stimulated |
| 1 | 0.4 | 0.15 |
| 2 | 4.5 | 1.5 |
| 3 | 30 | 4 |
| 5 | 0.2 | 0.1 |
| 6 | 5.5 | 3 |
| 8 | 6 | 3 |
| 12 | 0.2 | 0.1 |
| 13 | 0.35 | 0.4 |
| 14 | 0.55 | 0.3 |
| 15 | 0.7 | 0.45 |
| 16 | 0.7 | 0.2 |
| 17 | 4.5 | 4 |
| 18 | 5.5 | 2 |
| 19 | 7 | 2.5 |
| 20 | 4.5 | 2.5 |
| 21 | 0.7 | 0.3 |
| 22 | 0.8 | 0.25 |
| 32 | 6 | 2 |

We claim:

1. Compound of the formula I,

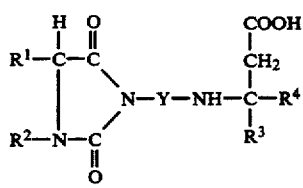

in which

Y denotes —$(CH_2)_m$—CO— or

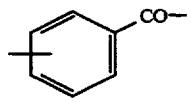

and m represents 1–4;

$R^1$ represents —$(CH_2)_n$—NH—X, —$CH_2$—$C_6H_4$—NH—X, —$CH_2$—$C_6H_4$—C(=NH)—$NH_2$, —$CH_2$—$C_6H_4$—$CH_2$—NH—X or —$C_6H_4$NH—X, or

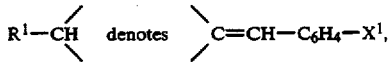

wherein n represents an integer from 3 to 5, $X^1$ represents —$CH_2$NHX, —NHX or —C(=NH)—$NH_2$, X represents hydrogen or $C_1$–$C_6$-alkyl, or represents a radical of the formula II,

wherein

R' and R" independently of one another denote hydrogen or $C_1$–$C_6$-alkyl;

$R^2$ denotes hydrogen or $C_1$–$C_6$-alkyl;

$R^3$ denotes hydrogen or a phenyl radical;

$R^4$ denotes hydrogen, $COOR^5$, CO—N($CH_3$)—$R^5$ or CO-NH-$R^5$, wherein $R^5$ denotes hydrogen, NHCO—$NH_2$ or ($C_1$–$C_{18}$)-alkyl, which is optionally mono- or polysubstituted by identical or different radicals from the series comprising hydroxyl, carboxyl, carboxamido, amino, mercapto, ($C_1$~$C_{18}$)-alkoxy, ($C_1$–$C_{18}$)-alkoxycarbonyl, ($C_6$–$C_{14}$)-aryl-($C_1$–$C_8$)-alkoxycarbonyl, ($C_3$–$C_8$)-cycloalkyl, halogen, nitro, trifluoromethyl and a radical $R^6$, wherein $R^6$ represents ($C_6$–$C_{14}$)-aryl, ($C_6$–$C_{14}$)-aryl-($C_1$–$C_8$)-alkyl, or a mono- or bicyclic 5- to 12-membered heterocyclic ring which can be aromatic, partly hydrogenated or completely hydrogenated and can contain, as a hetero element, one, two or three identical or different nitrogen, oxygen or sulphur atoms, the aryl and, independently of one another, the heterocyclic radical optionally being mono- or polysubstituted by identical or different radicals from the series comprising ($C_1$–$C_{18}$)-alkyl, ($C_1$–$C_{18}$)-alkoxy, halogen, nitro and trifluoromethyl; or $R^6$ represents a radical $R^7$;

$R^7$ denotes —$NR^8R^9$, —$OR^8$, —$SR^8$ or an amino acid side chain; or a naturally occurring or unnatural amino acid radical, imino acid radical or optionally N-($C_1$–$C_8$)-alkylated or ($C_6$–$C_{14}$)-aryl-($C_1$–$C_8$)-alkylated azaamino acid radical or a dipeptide radical, in which the peptide bond can be reduced to NH—$CH_2$, and esters and amides thereof, it being possible for free functional groups optionally to be substituted by hydrogen or hydroxy- methyl or protected by protective groups customary in peptide chemistry; or denotes a radical —$COR^{7'}$, wherein $R^{7'}$ is defined as $R^7$;

$R^8$ denotes hydrogen, optionally amino-substituted-($C_1$-$C_{14}$)-aryl-($C_1$-$C_8$)-alkyl, ($C_1$-$C_{18}$)-alkylcarbonyl, ($C_1$-$C_{18}$)-alkoxycarbonyl, ($C_6$-$C_{14}$)-arylcarbonyl, ($C_6$-$C_{12}$)-aryl-($C_1$-$C_8$)-alkylcarbonyl, ($C_6$-$C_{18}$)-aryl-($C_1$-$C_{18}$)-alkoxycarbonyl, or a naturally occurring or unnatural amino acid radical, imino acid radical or optionally N-($C_1$-$C_8$)-alkylated or ($C_6$-$C_{14}$)-aryl-($C_1$-$C_6$)-alkylated azaamino acid radical or a dipeptide radical, in which the peptide bond can be reduced to $NH$-$CH_2$; and $R^9$ denotes hydrogen, ($C_1$-$C_{18}$)-alkyl, ($C_6$-$C_{12}$)-aryl or ($C_6$-$C_{12}$)-aryl-($C_1$-$C_8$)-alkyl;

and/or physiologically tolerated salts thereof, excluding compounds of the formula I wherein, simultaneously, $R^1$ denotes —$(CH_2)_n$—NH—X, and Y denotes —$(CH_2)_m$—CO—.

2. Compound of the formula I according to claim 1, wherein $R^1$ denotes —$CH_2$—$C_6H_4$—C(NH)—$NH_2$ or —$CH_2$—$C_6H_4$—$CH_2$—$NH_2$, $R^2$ denotes H or $CH_3$, Y denotes —$CH_2$—CO— and $R^4$ denotes —CO—NH—$R^5$ wherein NH—$R^5$ represents an α-amino acid radical.

3. Compound of the formula I according to claim 1 wherein NH-$R^5$ represents a valine or phenylglycine radical.

4. A method for the inhibition of platelet aggregation which comprises administration of an effective amount of a compound of the formula I as claimed in claim 1.

5. A pharmaceutical composition for the inhibition of platelet aggregation comprising an effective amount of a compound of the formula I as claimed in claim 1 and a pharmaceutically acceptable vehicle.

6. A pharmaceutical composition for the inhibition of the bonding of osteoclasts to the bone surface comprising an effective amount of a compound of the formula I as claimed in claim 1 and a pharmaceutically acceptable vehicle.

* * * * *

UNITED STATES PATENT AND TRADEMARK OFFICE
CERTIFICATE OF CORRECTION

PATENT NO. : 5,389,614
DATED : Feb. 14, 1995
INVENTOR(S) : Konig et al.

It is certified that error appears in the above-identified patent and that said Letters Patent is hereby corrected as shown below:

Col. 1, lines 34-35, "$-CH_2-C_6H4-$" should read -- $-CH_2-C_6H_4-$ --;

Col. 1, line 42, "-NBX" should read -- -NHX --;

Col. 1, line 65, "$-C_6-C_8alkyl,$" should read -- $-C_1-C_8-alkyl,$ --;

Col. 2, line 11, "$C_5-C_{14}-aryl$" should read -- $C_6-C_{14}-aryl$ --;

Col. 2, line 25, "$C_1-C_{14}-aryl$" should read -- $C_5-C_{14}-aryl$ --;

Col. 3, line 14 "2 ben-" should read -- 2-ben- --:

Col. 3 line 30, "a Ala" should read -- ΔAla --;

Col. 3, line 32, "(Cys)2" should -- $(Cys)_2$ --;

Col. 3, line 34, "Guy" should read -- Guv --;

Col. 3, line 37, "a Lys" should read -- Δ Lys --;

Col. 3, line 62, "[2.2.2loctane)" should read [2.2.2] octane --;

Col. 7, line 66, "→" should be moved to Col. 8, line 5 to designate the structure thereon;

UNITED STATES PATENT AND TRADEMARK OFFICE
CERTIFICATE OF CORRECTION

PATENT NO. : 5,389,614
DATED : Feb. 14, 1995
INVENTOR(S) : Konig et al.

It is certified that error appears in the above-identified patent and that said Letters Patent is hereby corrected as shown below:

Col. 9, line 18, "IIIa" should follow the arrow on line 15;
Col. 9, line 50, the structure should read:

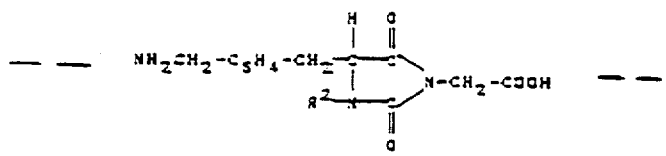

Col. 12, line 15, "Gel-filtereed" should read -- Gel-filtered --;
Col. 14, line 7, "N-ethyimorpholine" should read -- N-ethylmorpholine --;
Col. 14, line 68, "-24" should read -- -24° --;
Col. 15, line 17, "NarCO$_3$" should read -- NaHCO$_3$ --;
Col. 19, line 13, "for hours" should read -- for 5 hours --;
Col 19, line 39, "nitor" should read -- nitro --;
Col. 20, line 34, "safcosine" should read -- sarcosine --;
Col. 23, line 63, "yl)aspartyl" should read -- yl)-benzoyl-L-aspartyl --;
Col. 23, line 65, delete "acetyl-";
Col. 24, line 19, "-17.4°" should read -- =-17.4° --;

UNITED STATES PATENT AND TRADEMARK OFFICE
CERTIFICATE OF CORRECTION

PATENT NO. : 5,389,614
DATED : Feb. 14, 1995
INVENTOR(S) : Konig et al.

It is certified that error appears in the above-identified patent and that said Letters Patent is hereby corrected as shown below:

Col. 24, line 27, "-18.9°" should read -- =-18.9° --;

Col. 28, line 40, "$(C_1-C_{18})$alkoxy" should read -- $(C_1-C_{18})$-alkoxy --;

Col. 29, line 8, "-$(C_1-C_6)$-" should read -- -$(C_1-C_8)$- --;

Signed and Sealed this

Sixteenth Day of May, 1995

Attest:

BRUCE LEHMAN

*Attesting Officer*      *Commissioner of Patents and Trademarks*